United States Patent [19]

Trasch et al.

[11] Patent Number: 4,638,023
[45] Date of Patent: Jan. 20, 1987

[54] PROCESS FOR THE PRODUCTION OF REAGENT FILMS AND REAGENT FILMS PRODUCED THEREBY

[75] Inventors: Heinz-Freidrich Trasch, Ludwigshafen; Anselm Rothe, Birkenau; Bernward Sojka, Viernheim; Wolfgang Werner, Mannheim; Hans Wielinger, Weinheim, all of Fed. Rep. of Germany

[73] Assignee: Boehringer Mannheim GmbH, Mannheim, Fed. Rep. of Germany

[21] Appl. No.: 701,089

[22] Filed: Feb. 13, 1985

[30] Foreign Application Priority Data

Feb. 22, 1984 [DE] Fed. Rep. of Germany ....... 3406328

[51] Int. Cl.$^4$ ..................... G01N 31/22; G01N 33/52
[52] U.S. Cl. ........................................ 524/21; 524/17; 524/22; 524/23; 524/24; 524/379; 524/385; 427/2; 427/288; 428/289; 428/290

[58] Field of Search ....................... 524/17, 18, 21, 22, 524/23, 24, 379, 385; 427/2, 256, 288; 428/142, 289, 290; 106/125, 135, 149, 153; 260/123.7; 350/353, 354, 356, 357

[56] References Cited

U.S. PATENT DOCUMENTS 3,635,713  1/1972  Van Paesschen et al. ........... 524/17

FOREIGN PATENT DOCUMENTS 0960196  9/1982  U.S.S.R. ............................... 524/21

Primary Examiner—John Kight
Assistant Examiner—Nathan M. Nutter
Attorney, Agent, or Firm—Felfe & Lynch

[57] ABSTRACT

The present invention provides a process for the production of reagent films in which an aqueous synthetic resin dispersion which contains the usual adjuvants and reagents is coated on to a solid substrate or on to a thin fabric in a thin layer and dried, wherein to the crude film mass used for the coating there are added 0.5 to 5% by weight of a scleroprotein hydrolysate with a molecular weight of from 5000 to 50,000 and 0.5 to 10% by weight of a higher alcohol containing 5 to 10 carbon atoms.

7 Claims, No Drawings

PROCESS FOR THE PRODUCTION OF REAGENT FILMS AND REAGENT FILMS PRODUCED THEREBY

The present invention is concerned with a process for the production of reagent films, and with reagent films produced thereby.

In the case of the production of crude film masses which are to be further worked up to give optical films and especially to give reagent films, the following conditions are to be observed: during the whole of the further working up process, the crude film mass is to have the same physical consistency, i.e. during a discrete standing time, it must not partly demix due to sedimentation of incorporated particles. If a partial demixing takes place, then during the coating period, which on a technical scale can amount to several seconds, homogeneity within a batch cannot be guaranteed.

Furthermore, it can only be avoided by technically laborious measures that during the production procedure air is not stirred into the crude material mass. Normally, this stirred-in air must, therefore, be removed before the coating procedure in order that no foam bubbles are formed which result in inhomogeneities in the coating film.

According to the present state of the art, only by means of a relatively expensive apparatus can a mass be worked up which sediments in the case of standing for a comparatively long period of time; this takes place by continuous stirring and circulatory pumping of the mass. In the case of this procedure, freedom from foaming can be achieved by evacuation of the reactor.

Consequently, it is an object of the present invention to provide a simpler process for the production and preservation of crude film masses.

Hitherto, attempts have certainly not been lacking to avoid the deposition of coating masses, as well as to reduce or prevent foam formation. For this purpose, the following measures are known:

The deposition of the coating masses can generally be prevented by the addition of viscosity-increasing substances, such as alginates, dextrans, water-swellable cellulose derivatives and the like, or dispersion agents, such as polyvinyl alcohols, polyacrylamides, completely or partly saponified polyvinyl acetates, polyvinylpyrrolidones, higher fatty acids (for example stearic acid) or the salts thereof or higher alcohols (for example cetyl alcohol), which can be branched or non-branched. Such additives or the increase of the viscosity thereby brought about lead, however, to difficulties in the further working up. The foam formation of the crude film masses can be reduced or prevented by the addition of known antifoaming agents, alcohols, alkanes and the like.

In the case of the production of reagent films based on synthetic resin dispersions according to U.S. Pat. No. 3,630,957 it has proved to be favourable to increase the permeability or absorbability thereof by incorporating pigments and/or particles with large surface areas, such as diatomaceous earth, titanium dioxide or silicon dioxide, into the film mass. It is obvious that, in the case of the casting and/or drawing of such films, the crude film mass must be free of bubbles or that during the whole of the production procedure a deposition of the filling materials is avoided.

In the same way, in the case of the production of reagent films according to Federal Republic of Germany Patent Application No. P 32 47 608.6, it is necessary that the crude film mass has a consistency by means of which, on the fabric substrate used, there is formed a film with constant wet film thickness, without this penetrating through the fabric. This deposition and also the penetration can, in general, be controlled by increasing the viscosity of the coating mass. Viscosity-increasing agents are admittedly permissible for reagent film crude masses or for reagen films in relatively low concentrations but, when they are used in comparatively large amounts, they have the disadvantage that, due to them, the percentage proportion of the porous filler materials/openers is reduced and, furthermore, chemical-biochemical reactions taking place in the film in the case of the detection reactions are negatively influenced. These disturbances are characterised in that the liquid take up in the reagent film is slowed down and thus the required reaction time is prolonged. Furthermore, a hydrophobing of the film can occur and the enzyme activity employed cannot be fully effective.

Therefore, it is an object of the present invention to provide a process for the production of reagent films, which are produced on the basis of synthetic resin dispersions, which minimises foam formation, retains the hydrophilic properties of the reagent film and, at the same time, without disturbing the viscosity increase, suppresses the deposition of the necessary filling materials during the production and working up process, including a centrifuging step, for the crude film masses, as well as prevents a penetration of the wet crude film mass when it is applied to a fabric substrate.

Surprisingly, we have found that a combination of an alcohol containing 5 to 10 carbon atoms, for example hexanol or isoamyl alcohol, which are known as defoaming agents, with a water-soluble scleroprotein hydrolysate with a molecular weight of from 5000 to 50,000 and preferably of from 5000 to 20,000 (for example crotein C from collagen, crolastin from elastin, gelatine and the like), which are added in a mixing ratio of from 0.5 to 10% by weight of alcohol and 0.5 to 5% by weight of protein hydrolysate to the coating mass, imparts thereto the good properties set out above in the statement of the object of the present invention.

Thus, according to the present invention, there is provided a process for the production of reagent films in which an aqueous synthetic resin dispersion which contains the usual adjuvants and reagents is coated on to a solid substrate or on to a thin fabric in a thin layer and dried, wherein to the crude film mass used for the coating there are added 0.5 to 5% by weight of a scleroprotein hydrolysate with a molecular weight of from 5000 to 50,000 and 0.5 to 10% by weight of a higher alcohol containing 5 to 10 carbon atoms.

In the case of the production of these reagent films, it is possible to proceed as follows: to an aqueous synthetic resin dispersion are added the conventional adjuvants, especially high molecular weight swelling agents, such as alginates, various substituted, water-swellable cellulose derivatives, dextran, polyacrylic acids, polyethylene glycol, fully or partly saponified polyvinyl acetates, polyvinylpyrrolidones and the like. Into this are incorporated the enzymes, indicators, buffers and possibly wetting agents necessary for the detection reaction, such as are described, for example, in Federal Republic of Germany Patent Specification No. 1,598,153. In addition, for the acceleration of the detection reaction (acceleration of the take up of serum), filling materials, such as diatomaceous earth, cellulose or the like, as well as detergents, are incorporated. Without the additives according to the present invention, such crude film masses cannot be worked up without problems since foam formation and deposition of the filling materials takes place, possibly partly before but always during the centrifuging necessary for the removal of the foam and, in the case of a working up according to Federal Republic of Germany Patent Specification No. P 32 47 608.6, a penetration of the coating mass through the fabric to be coated also occurs.

By the addition of, for example crotein C alone to the crude film mass, the desired effect is not achieved and it also cannot be achieved by the addition of higher alcohols alone, for example hexan-1-ol.

It is surprising that the mixtures used according to the present invention of scleroprotein hydrolysates, together with higher alcohols, which hitherto have not been known as suspension or dispersion adjuvants, bring about, in the combination according to the present invention, on the one hand, the stabilisation of the suspension against demixing, which is necessary for the working up, and, on the other hand, however, in the case of air drawn in during the working up, liberated it again without any problems and without foam formation so that homogeneous, bubble-free crude film masses are obtained. Other viscosity-increasing materials or other defoaming agents, even in combination with one another, do not give the optimum results obtained according to the present invention.

As a basis for the crude film masses, there can be used, for example, the aqueous synthetic resin dispersions already known from Federal Republic of Germany Patent Specification No. 1,598,153. By way of example, as synthetic resins there may be mentioned polyvinyl acetate, polyvinyl propionate, polyacrylate, polymethacrylate or co-polymers thereof, as well as polyamides, polystyrene, polyalkylenes and the like. The proportion of synthetic resin in the dispersion is usually from 20 to 60% by weight.

The following Examples are given for the purpose of illustrating the present invention:

EXAMPLE 1

A generally usable crude film mass composition can comprise:
35 KU glucose oxidase
200 KU peroxidase
15 ml. 0.5M phosphate buffer (pH 5)
0.3 g. sodium alginate
25 g. of a dispersion of a co-polymer of vinyl acetate and vinyl propionate (50% in water)
0.5 g. 3,3′,5,5′-tetramethylbenzidine
0.2 g. phenyl semicarbazide
1 g. dioctyl sodium sulphosuccinate
6 ml. methoxyethanol
20 g. titanium dioxide
35 ml. water Into the crude film mass were incorporated the amounts of crotein C and hexan-1-ol stated in the following Table 1:

TABLE 1

| % proportion of higher alcohol in the crude film mass | % proportion of crotein C in the crude film mass | disturbances | | |
|---|---|---|---|---|
| | | foam formation | deposition of filling materials | penetration of the coating mass |
| 0 | 0 | strong | + | + |
| 1 | 0 | slight | + | + |
| 2 | 0 | none | + | + |
| 5 | 0 | none | + | + |
| 1 | 1 | slight | + | + |
| 1 | 2 | slight | − | − |
| 2 | 2 | none | − | − |
| 0 | 2 | strong | − | − |
| 3 | 3 | none | − | − |

+ = recognisable disturbance
− = no recognisable disturbance.

Foam formation and deposition of filling materials were tested for visually and penetration by the coating mass was tested for after coating a multifilar polyamide fabric 2 F 131 (Schweizer Seidengazefabrik, Thal) with a wet film thickness of 200 μm. by subsequent observation of the under side of the fabric.

It is thus shown that the additives can be chosen, according to need, over a wide range of concentrations. The effects which are to be achieved by the process according to the present invention can also by accomplished in an appropriate manner by means of other higher alcohols and other scleroproteins or scleroprotein hydrolysates.

EXAMPLE 2

Test for the detection of glucose in blood/serum/plasma

35 KU glucose oxidase
200 KU peroxidase
1.5 g. crotein C
35 ml. double distilled water
25 g. dispersion of a co-polymer of vinyl acetate and vinyl propionate (50% in water)
0.3 g. alginate
15 ml. 0.5M phosphate buffer (pH 5)
0.5 g. 3,3′,5,5′-tetramethylbenzidine
0.2 g. phenyl semicarbazide
6 ml. methoxyethanol
1 g. dioctyl sodium sulphosuccinate
2.0 ml. isoamyl alcohol
20 g. titanium dioxide
were worked up to give a homogeneous mass and coated with a width of 0.15 mm. on to a 250 μm. thick multifilar polyamide fabric (2 F 131, Schweizer Seidengazefabrik, Thal) and dried.

During the preparation of the mass to be used for the coating, stirred-in air was removed by centrifuging at 200–250 g. After centrifuging, no enrichment of filling materials on the bottom of the centrifuging vessel was observed. A foam formation was also not observed.

The mass was coated continuously on to the multifilar polyamide fabric, a penetration of the fabric by the mass thereby not being observed.

The dried, coated fabric was cut up into strips with a width of 5 mm. These were then, together with a 5 mm. wide strip of filter paper hydrophobed with silicone oil, fixed by means of a thin nylon mesh (filament gauge 40μ, mesh width 50μ) on to a 250μ thick and 8 to 10 cm. wide supporting film so that the paper lay directly on the supporting film and the fabric came to lie with the film side upwardly. The nylon mesh was stuck on to the supporting flim besides these strips so that, by its tension, the strips were firmly held about 5 mm. from the edge of the supporting film. Thereafter, the whole laminate was cut up into test strips of 5 mm. width.

Upon moistening with serum, these strips gave a uniform green to blue colour reaction, depending upon the glucose concentration.

EXAMPLE 3

Test for the detection of glucose in urine

40 KU glucose oxidase
160 KU peroxidase
2 g. reticusol
10 ml. 1M citrate buffer (pH 5)
0.25 g. sodium alginate
30 g. dispersion of co-polymer of vinyl acetate and vinyl propionate (50% in water)
0.7 g. 3,3',5,5'-tetramethylbenzidine
0.2 g. phenyl semicarbazide
10 ml. methanol
1 g. dioctyl sodium sulphosuccinate
20 g. silica gel
25 ml. water
4 ml. hexan-1-ol
were worked up to give a homogeneous mass and coated with a strip width of 0.1 mm. on to a 350 μm. thick polyester fleece (DuPont/Remey 2033) and dried. The carrier thus obtained was further worked up to give test strips in the manner described in Example 2.

Due to the high proportion of hexanol, it was not necessary to centrifuge the mass since virtually no air was included in the mass. A sedimentation of filling materials up to a standing time of 6 hours was not observed.

The mass could be satisfactorily coated on to fabrics and fleece without penetration.

EXAMPLE 4

Test for the detection of uric acid in blood

40 KU peroxidase
1 KU uricase
1.0 g. crolastin
20 g. dispersion of a co-polymer of vinyl acetate and vinyl propionate (50% in water)
0.25 g. sodium alginate
0.5 g. non-ionic wetting agent
0.05 g. sodium ethylenediamine-tetraacetate
3 ml. isobutanol
20 g. kieselguhr
20 ml. 0.2M phosphate buffer (pH 7)
0.4 g. primaquine diphosphate
18 ml. water
were worked up to give a homogeneous mass and coated with a strip width of 0.2 mm. on to a 140 μm. thick polycarbonate film (Pokalon K, one side matt, Lonza, Weil am Rhein) and dried. Further working up to give test strips took place in a manner analogous to that described in Example 2.

The mass employed could be centrifuged and showed no deposition of filling materials at 250 g. Foam formation was also not observed.

EXAMPLE 5

Comparison of various scleroprotein hydrolysates

Formulation 20 g. sodium alginate (1.7% in 0.5M phosphate buffer; pH 5)
30 g. dispersion of a co-polymer of vinyl acetate and vinyl propionate (50% in water)
10 g. dodecylbenzene-sulphonate (15% in water)
20 g. cellulose powder
8 g. methoxyethanol
0.7 g. hexan-1-ol
1.4 g. scleroprotein hydrolysate
21.5 g. water.

The above components were thoroughly mixed with a rapidly running stirrer and any air stirred in during the mixing was moved to the surface by centrifuging at 200 to 250 g. Foam formation and a possible formation of sediment, as well as density and viscosity of the mixture, were subsequently determined. The mass was thereafter coated as in Example 1 on to a multifilar polyamide fabric and the penetration into the substrate, as well as the quality of the coating remaining behind after dying, were assessed. The experimental results are summarized in the following Table 2. It can be seen that high molecular weight protein hydrolysates (gelatines A+B), which are only soluble in hot water, very considerably increased the viscosity of the mixture and, on the one hand, resulted in foam formation and, on the other hand, did not give smooth films. In contradistinction thereto, cold soluble hydrolysates displayed neither foam formation nor a sedimentation and gave rise to smooth films.

In the following Table 2:
−=no finding
+=slight finding
++=clear finding
+++=strong finding.

TABLE 2

| | foam | sediment | penetration during coating | coating | density | viscosity |
|---|---|---|---|---|---|---|
| gelatine A M.W. 100,000 acid digested | ++ | − | − | orange-skin formation | 1.1604 | 556.8 mPas 212% |
| gelatine B M.W. about 100,000 alkaline digested | ++ | − | − | slight orange-skin formation | 1.1619 | 489.1 mPas 186% |
| gelatine ASF M.W. 10,000–20,000 | + | − | (+) | clear coating, smooth surface | 1.1618 | 228.7 mPas 87% |
| gelatine GSD M.W. 5000–30,000 | + | − | + slight penetration directly after | surface structured by the substrate | 1.1573 | 236.8 mPas 90% |

TABLE 2-continued

| | foam | sediment | penetration during coating | coating | density | viscosity |
|---|---|---|---|---|---|---|
| croteines | + | — | coating — | surface structured by the substrate | 1.1614 | 262.6 mPas 100% |

We claim:

1. In a process for the production of reagent films of the type comprising applying a coating of an aqueous synthetic resin dispersion which contains adjuvants and reagents onto a solid substrate or onto a thin fabric in a thin layer, and thereafter drying said thin layer on said substrate or fabric;

the improvement comprising:
adding to the aqueous synthetic resin dispersion used for the coating, 0.5 to 5% by weight of a scleroprotein hydrolysate with a molecular weight of from 5000 to 50,000 which is cold soluble in said dispersion and 0.5 to 10% by weight of a higher alcohol containing 5 to 10 carbon atoms.

2. The process according to claim 1, wherein the scleroprotein hydrolysate used is selected from the group consisting of a collagen and elastin hydrolysate.

3. The process according to claim 2, wherein the scleroprotein hydrolysate used is selected from the group consisting of a crotein C and crolastin.

4. The process according to claim 1, wherein the alcohol used is selected from the group consisting of hexanol and isoamyl alcohol.

5. The process of claim 1 wherein the scleroprotein hydrolysate used is selected from the group consisting of a collagen and elastin hydrolysate and wherein the alcohol used is selected from the group consisting of hexanol and isoamyl alcohol.

6. In a crude film mass for the production of reagent films comprising an aqueous synthetic resin dispersion and adjuvants and reagents, the improvement comprising from 0.5 to 5% weight of scleroprotein hydrolysate with a molecular weight of from 5000 to 50,000 and 0.5 to 10% by weight of an alcohol containing 5 to 10 carbon atoms.

7. The crude film mass according to claim 6, wherein the adjuvants present are selected from the group consisting of swelling agents, buffers, wetting agents, emulsifiers and viscosity-regulating materials.

* * * * *